(12) United States Patent
Sohar

(10) Patent No.: US 9,880,113 B2
(45) Date of Patent: Jan. 30, 2018

(54) METHOD OF X-RAY NANO-RADIOGRAPHY AND NANOTOMOGRAPHY AND A DEVICE FOR EXECUTING THIS METHOD

(71) Applicant: ADVACAM s.r.o., Praha (CZ)

(72) Inventor: Jan Sohar, Hýskov (CZ)

(73) Assignee: ADVACAM S.R.O., Prague (CZ)

( * ) Notice: Subject to any disclaimer, the term of this patent is extended or adjusted under 35 U.S.C. 154(b) by 0 days.

(21) Appl. No.: 15/531,467

(22) PCT Filed: Dec. 3, 2015

(86) PCT No.: PCT/CZ2015/000145
§ 371 (c)(1),
(2) Date: May 30, 2017

(87) PCT Pub. No.: WO2016/086908
PCT Pub. Date: Jun. 9, 2016

(65) Prior Publication Data
US 2017/0269009 A1    Sep. 21, 2017

(30) Foreign Application Priority Data

Dec. 3, 2014   (CZ) ..................... 2014-852

(51) Int. Cl.
*G01N 23/00* (2006.01)
*G01N 23/04* (2006.01)
*G01N 23/225* (2006.01)

(52) U.S. Cl.
CPC ....... *G01N 23/046* (2013.01); *G01N 23/2251* (2013.01); *G01N 2223/045* (2013.01); *G01N 2223/419* (2013.01)

(58) Field of Classification Search
CPC ............. G01N 23/046; G01N 23/2251; G01N 2223/419; G01N 2223/045
(Continued)

(56) References Cited

U.S. PATENT DOCUMENTS

2007/0071164 A1    3/2007  Shu et al.
2009/0065708 A1    3/2009  Moon et al.
(Continued)

FOREIGN PATENT DOCUMENTS

EP    2708874 A1    3/2014
JP    2012-43563 A  3/2012
WO   2014/006443 A2  1/2014

OTHER PUBLICATIONS

Franziska Schmidt et al: "From 2D Slices to 3D Volumes: Image Based Reconstruction Hippocampal Cells on Charged and Uncharged Surfaces Using FIB/SEM Serial Sectioning", Ultramicroscopy, Elsevier, Amsterdam, NL, vol. 111, No. 4, Dec. 24, 2010, pp. 259-266, SP028153008, ISSN; 0304-3991, DOI: 10.1016/J.Ultramic.2010.12.017.
(Continued)

*Primary Examiner* — Michael Maskell
(74) *Attorney, Agent, or Firm* — Mark M. Friedman

(57) ABSTRACT

The invention describes a method and a device (9) for executing a method of X-ray nano-radiography and nano-tomography using a scanning electron microscope (1) consisting of the focus of an electron beam (2) from an electron microscope (1) onto one point of the surface of a scanned sample (3), the emission of bremsstrahlung and fluorescent radiation (6) from the focal point of the impact of the electron beam (2), the sensing of the scanned sample (3), and recording an image of the structure of the scanned sample (3) based on the change of intensities of the bremsstrahlung and fluorescent radiation (6) by the imaging detector (7) arranged behind the sample (3).

7 Claims, 3 Drawing Sheets

(58) Field of Classification Search
USPC .................................. 250/306, 307, 310, 311
See application file for complete search history.

(56) References Cited

U.S. PATENT DOCUMENTS

| | | |
|---|---|---|
| 2013/0195242 A1 | 8/2013 | Iwamoto |
| 2013/0287177 A1* | 10/2013 | Funk .................. A61B 6/4064 378/141 |
| 2014/0183357 A1* | 7/2014 | Smith ................ G01N 23/2252 250/307 |
| 2016/0189922 A1* | 6/2016 | Kooijman ............. H01J 37/244 250/307 |

OTHER PUBLICATIONS

Hossein Ostadi et al: "3D Visualization and Characterization of Nano Structured Materials", Nanotechnology (IEEE-NANO), 2011 11TH IEEE Conference on, IEEE, Aug. 15, 2011, pp. 770-775, XP032105311, DOI: 10.1109/NANO.2011.6144402 ISBN: 978-1-4577-1514-3, Chapter 11.
Russell Sara S et al: "The Texture of a Fine-Grained Clacium-Aluminium-Rich Inclusion (CAI) in Three Dimensions and Implications for Early Solar System Condensa", Geochimica Et Cosmochimica ACTA, vol. 116, Apr. 18, 2013, pp. 51-62, SP028680358, ISSN: 0016-7037,DOI:10.1016/J.GCA.2013.04.007 Chapters 2.1 and 2.2; Figure 1.
Vanhecke, D., et al: J. Struct. Biol 159 (2007), 443-450, Whole Document.

* cited by examiner

METHOD OF X-RAY NANO-RADIOGRAPHY AND NANOTOMOGRAPHY AND A DEVICE FOR EXECUTING THIS METHOD

FIELD OF THE INVENTION

The invention relates to a method and a device for executing nano-radiography and nanotomography using a scanning electron microscope. The invention allows for the creation of a surface model, including an exact model of the internal structure of the scanned sample.

BACKGROUND OF THE INVENTION

Scanning electron microscopes are used to map the surface of a scanned sample with a precision in the order of nanometers. Scanning electron microscopes usually include an electron source which generates electron beams. Using electron optics, the electron beam is focused on a single point on the surface of the scanned sample. Upon impact of the electron beam to the specified point of the sample, some electrons are reflected and/or secondary electrons are released and/or characteristic X-rays are emitted. These particles are recorded by at least one detector, while results state the values of the sample point of the surface of the sample to reflect or to emit secondary particles. The surface of the sample is scanned completely, point by point, then its image is created from the results.

During X-ray transmission radiography, the attenuation of the intensity of X-ray radiation passing through the sample is observed. An X-ray tube is used as a source of X-ray radiation. The sample is placed into the path of the X-rays. The X-rays subsequently impact upon the detector, which records their intensity. The result is an image that shows the internal structure of the sample in terms of its ability to attenuate X-rays.

If a larger set of images of the sample is recorded, taken under different irradiation angles, the method of computed tomography can be used to model a three-dimensional description of the internal structure of the scanned sample.

The task of the present invention is to create a method and a device that allows, within a single working operation, for the execution of nano-radiography, nanotomography, microscopy, and possibly the topography of the surface of the sample.

SUMMARY OF THE INVENTION

The invention objective is solved by the creation of a method and a device for executing nano-radiography and nanotomography through the use of a scanning electron microscope in accordance with this invention.

The method of X-ray nano-radiography and nanotomography using a scanning electron microscope first involves directing the electron beam emerging from the scanning electron microscope to a point on the scanned surface of the sample. This is followed by the detection of reflected and secondary particles by at least one detector, which also records data on the reflected and emission parameters of the given point. The method comprises repeating scanning for all points of the scanned surface of the sample.

The essence of the invention consists in that, simultaneously with the impact of the electron beam on a point on the scanned surface of the sample, bremsstrahlung and fluorescent radiation is emitted, wherein the point of impact is also the focal point of the thus emitted X-ray radiation. This X-ray radiation is emitted from the focal point in all directions and part of it also penetrates into the sample. The intensity of this radiation is partly attenuated by the sample according to the density and material distribution in the volume of the sample. X-ray radiation that is not attenuated and exits from the sample is detected by at least one imaging detector placed behind the sample. The image captured by this detector shows the internal structure of the sample, so the parts of the sample structure are differentiated according to theft ability to attenuate the X-rays passing through. This image is recorded repeatedly for all positions of the focal point on the sample surface and, using methods of computer tomography, the internal structure of the sample is modeled in 3D.

The function of the scanning electron microscope remains unchanged because the ability of the surface of the object to emit or reflect particles at a given point is still detected. What is newly used is the accompanying phenomenon in which bremsstrahlung X-ray radiation is released with the impact of the electron beam. This X-ray radiation is more penetrating than the electron beam, so it can pass through the entire volume of the sample. Behind the sample there is placed an imaging detector that records the image of changes in intensity of the transmitted X-ray radiation behind different parts of the sample. This creates a magnified image of the internal structure of the sample. The magnification of the individual parts of the structure of the sample depends on their distance from the focal point. The structures located just below the surface and thus close to the focal point are increased the most, and the resolution in their radiographic image, in this case, comes close to the resolution of electron microscopy and amounts to units in tens of nanometers. For this reason, the term nano-radiography is used.

When all the radiographic images thus recorded are taken at multiple positions of the focal point on the surface of the scanned sample, it is possible to use the data to calculate a three-dimensional model of the structure of the sample with a resolution of up to tens of nanometers. In this case the term nanotomography is relevant. Radiographic data are collected simultaneously with the scanning by the electron microscope.

In another preferred embodiment of the method of nano-radiography and nanotomography in accordance with the invention, a flat pattern object with known dimensions is placed into the space between the sample and the imaging detector. This pattern object may be, for example, a thin metal grid. During the course of radiographic imaging, the image of the known pattern object is superimposed on the image of the sample, wherein the magnification of the known sample depends on the distance of the focal point from the known pattern object. From the recorded image data, the level of magnification of the known pattern object can be determined, and the distance of the focal point from this pattern object can be subsequently calculated. This procedure is gradually applied to all of the positions of the focal point during scanning. The determined distances are used to comprise a 3D model of the shape of the surface of the sample, i.e. its topography. The determined shape of the surface of the sample can be subsequently used to improve the tomographic reconstruction of the sample.

Part of the invention is also a device for executing the aforementioned method.

The device for X-ray nano-radiography and nanotomography including a scanning electron microscope consists of an electron beam source, an electron optics for focusing the electron beam to a point on the surface of the scanned sample, followed by at least one detector for detecting reflected and secondary particles. The device also includes a control unit.

The essence of the invention consists in that the point on the surface of the scanned sample onto which the electron beam is focused is the focal point of the emission of the bremsstrahlung and fluorescent X-ray radiation. Furthermore, behind the sample there is located an imaging detector for detecting attenuation of the bremsstrahlung and fluorescent X-ray radiation in the sample and which is connected to the control unit.

The imaging detector is able to record a decrease in the intensity of the bremsstrahlung X-ray radiation. The results of the detection are sent to the control unit, which processes them into models. Bremsstrahlung radiation is an accompanying phenomenon, so it does not need its own source or independent optics.

In another preferred embodiment of the device for X-ray nano-radiography and nanotomography in accordance with the present invention, the control unit includes at least one module from the group of modules for storing data, a calculation module, a display module, a recording module, and a distribution module. The calculating unit comprises a computer. The module for data storage is realized by a data storage unit, the calculation module is realized by a processor, and the recording module is realized by a connected printer. The display module is a computer display and the distribution module is a network card that enables communication with remote systems. The modules can be implemented as virtual devices in the operating program of the computer.

In another preferred embodiment of the device for X-ray nano-radiography and nanotomography in accordance with the present invention, between the sample and the imaging detector there is arranged at least one pattern object with known dimensions, and the control unit is adapted to evaluate the magnification of the image of this sample. The image of attenuation of the intensity of the bremsstrahlung X-ray radiation of the pattern and its known dimensions avow for the calculation of the position of the focal point. The position of the focal point is important for further modeling of the sample, e.g. for topography of the sample surface.

The main advantages of the invention include high resolution and a time savings in the working operation. During a single scan, data for nanotomography, nano-radiography, and topography are determined, and the actual scanning of the surface by electron microscope is not affected.

DESCRIPTION OF THE DRAWINGS

The invention will be further illustrated by the following drawings, which show.

EXAMPLES OF THE PREFERRED
EMBODIMENTS OF THE INVENTION

It is understood that the individual specific examples of the realization of the invention are presented for illustrative purposes and not as a limitation of the invention to the cases shown herein. Experts who are familiar with the state of technology shall find, or using routine experimentation will be able to determine, many equivalents to the specific realizations of the invention which are specifically described here. These equivalents shall also be included into the scope of the patent claims.

Figure 1:
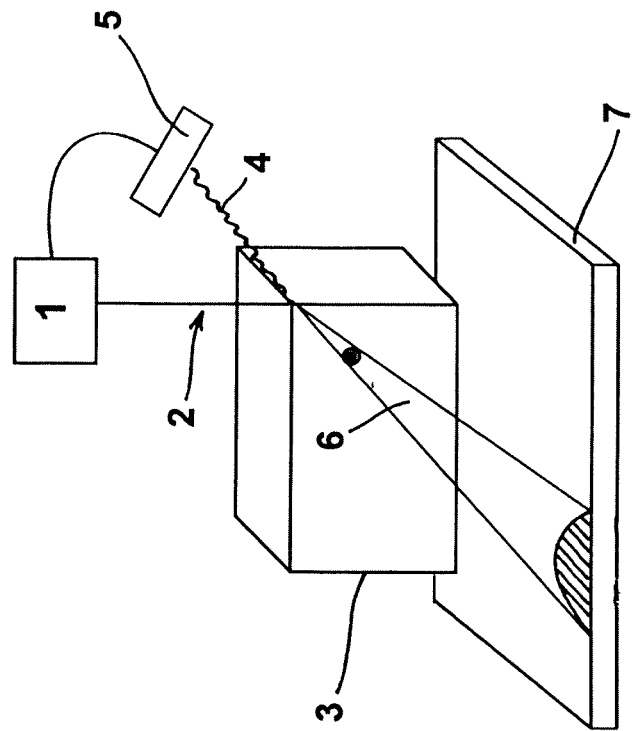
FIG. 1 a schematic representation of the change of the image of intensity of the bremsstrahlung X-ray radiation to a defect inside the sample according to the focal point of bremsstrahlung radiation, FIG. 2 a schematic representation of the device for topography of the surface of the sample, FIG. 3 a schematic representation of the device for nano-radiography and nanotomography.
Figure 1:
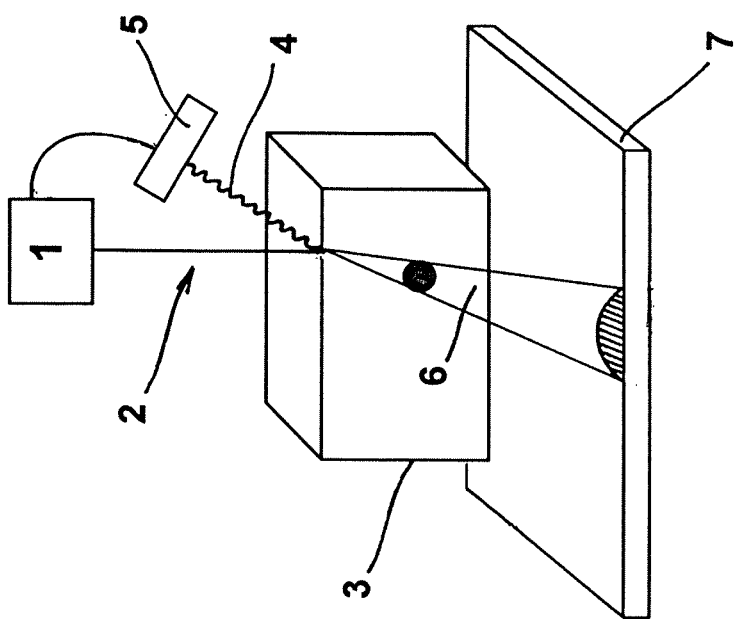
Figure 2:
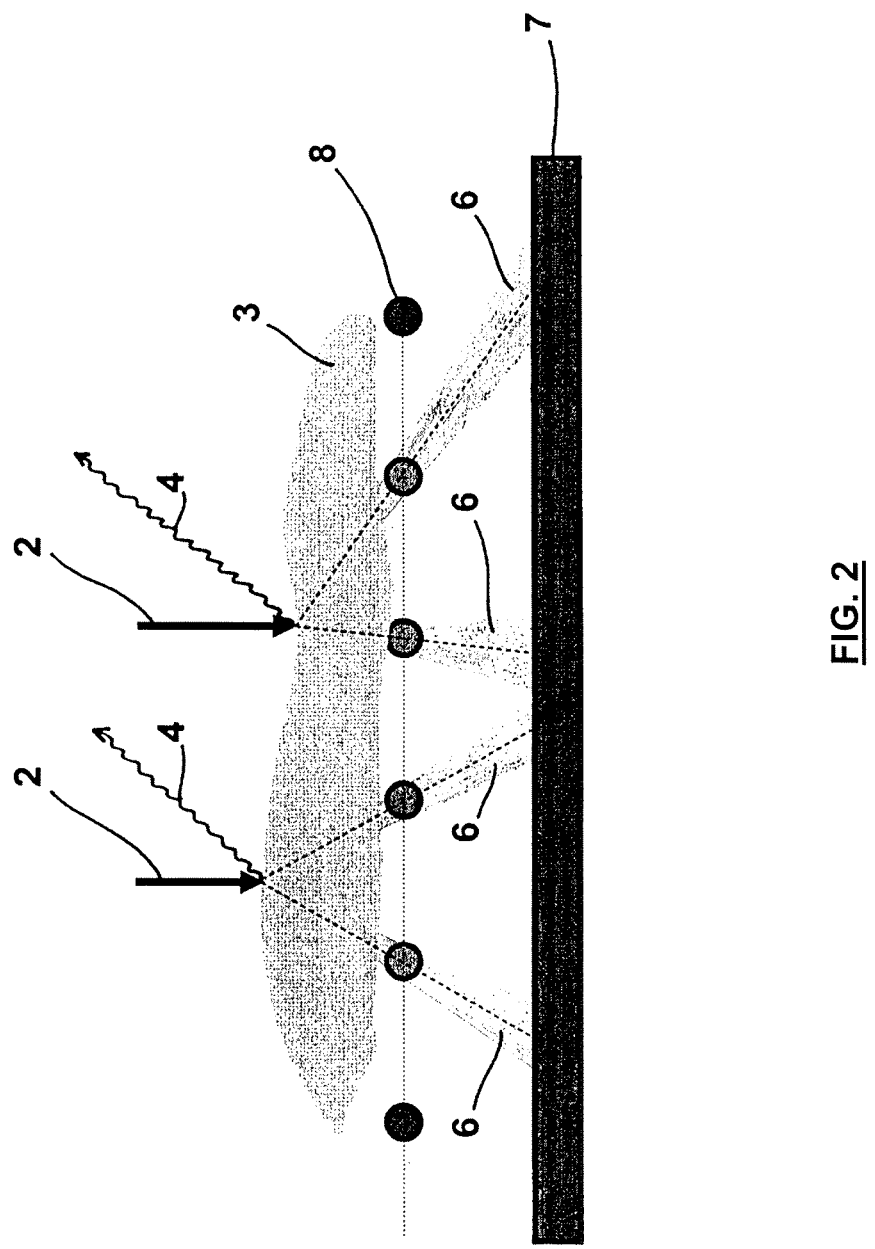
Figure 3:
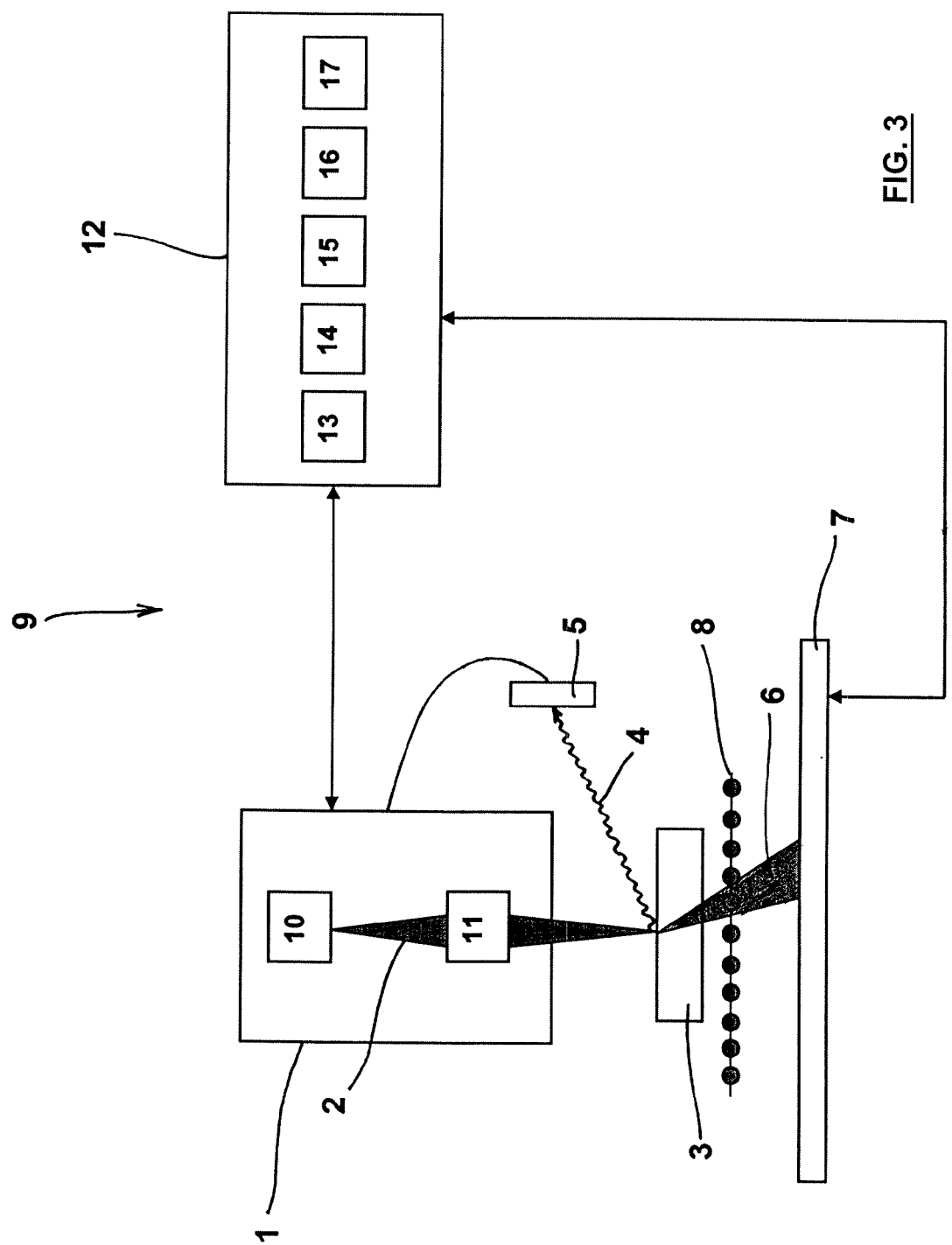

The invention is presented in FIG. 1, where the method of the invention's operation is schematically shown. The method uses a scanning electron microscope 1, inside which is generated an electron beam 2. The electron beam 2 is directed to a point on the surface of the scanned sample 3. From the point of impact there is generated secondary radiation 4 and reflected particles 4 which spread in all directions. This secondary radiation 4 is detected by at least one associated detector 5 of reflected and secondary particles 4 and from whose data the character of the sample 3 is determined at the point of impact.

The point of impact also forms a so-called focal point of bremsstrahlung and fluorescent radiation 6 from which the bremsstrahlung and fluorescent 6 radiation spreads into the space. This radiation 6 has high penetrability, so it penetrates the scanned sample 3. Behind the sample 3 in the direction of the advance of the bremsstrahlung radiation 6 there is arranged at least one imaging detector 7 which is able to record the intensity of the bremsstrahlung radiation 6. As soon as the sample 3 has an inhomogeneous structure in terms of the absorption of X-ray radiation 6, this internal structure affects the output intensity of the radiation 6 and the image of the internal structure of the scanned sample 3 is recorded on the detector 7.

If the focal point shifts (see FIG. 1), the output image also changes. From the set of images obtained in all positions of the focal point, a 3D model structure of the sample 3 is computed by computed tomography.

In order to model a three-dimensional model of the surface of the scanned sample 3, a pattern object 8 of known dimensions is arranged behind the scanned sample 3 in the direction of the bremsstrahlung radiation 6 from the focal point. An image of the structure of the sample 3 and the pattern object 8 is thus projected on the imaging detector 7 by the penetrating X-ray radiation. In a combined image, captured in this way, an image of the pattern 8 is identified and its enlargement is determined, for example, using the method of image correlation. From the known dimensions of the pattern 8 and the image of its attenuation of intensities of bremsstrahlung radiation 6 passing through the pattern 8 the distance of the focal point from the pattern object 8 is calculated and thus the height of the surface of the sample 3 at the scanned point. Through the arrangement of all scanned points next to each other, a 3D model of the surface of the specimen 3 is modeled.

The device 9 comprises a standard scanning electron microscope 1 having a source 10 of electron beam 2, electron optics 11 for directing and focusing the electron beam 2 and at least one associated detector 5 of reflected and secondary particles 4 from the scanned sample 3. Also, behind the scanned sample 3 in the direction of bremsstrahlung radiation 6 there is arranged a metal grid forming a pattern 8 of known dimensions and an imaging detector 7. The imaging detector 7 can be formed e.g. by a Timepix pixel detector.

The scanning electron microscope 1 and the imaging detector 7 are connected to a control unit 12 realized by a computer. The control unit 12 includes a module 13 for storing data. The module 13 consists of a data storage connected to a computer of the control unit 12. Part of the control unit 12 is also a calculation module 14, which consists of computing software means running in the operating system of the control unit 12. The calculation module 14 uses the processor of the computer. The display module 15 consists of a computer display and the recording module 16 consists of a printer connected to the computer. The distribution module 17 is composed of a network adapter for connecting to data networks for sharing data.

INDUSTRIAL APPLICABILITY

The invention shall find application in biological and medical applications, in applications testing the quality of products, in sectors dealing with new types of materials, in the semiconductor industry for testing chip quality, and in archeology and in other sectors where it is necessary to know the 3D internal structure of a sample, without damaging it.

OVERVIEW OF THE POSITIONS USED IN THE DRAWINGS 1 scanning electron microscope
2 electron beam
3 sample
4 reflected and secondary particles
5 detector of reflected and secondary particles
6 bremsstrahlung and fluorescent X-ray radiation
7 imaging detector
8 pattern object with known dimensions
9 device for X-ray nano-radiography and nanotomography using a scanning electron microscope
10 electron beam source
11 electron optics
12 control unit
13 module for data storage
14 calculation module
15 display module
16 recording module
17 distribution module

The invention claimed is:

1. A method for X-ray nano-radiography and nanotomography using a scanning electron microscope (1), first comprising the directing of an electron beam (2) projecting from a scanning electron microscope (1) to a point on the surface of a sample (3), further the detection of reflected and secondary particles (4) by least one detector (5) including the recording of data relating to the reflection and emission parameters of a given point, and further comprising repeating scanning at all points of the scanned surface of the sample (3), characterized in that, simultaneously with the impact of the electron beam (2) onto the point on the scanned surface of the sample (3) there is emitted bremsstrahlung and fluorescent X-ray radiation (6), wherein the impact point is also the focal point of the emitted bremsstrahlung and fluorescent X-ray radiation (6), and that the bremsstrahlung and fluorescent X-ray radiation (6) projecting from the sample (3) is detected by at least one imaging detector (7) arranged behind the sample (3), whereupon the image of attenuation of bremsstrahlung and/or fluorescent X-ray radiation (6) is recorded, and after the recording of the images of all focal points, the internal structure of the sample (3) is modeled using computer tomography.

2. A method according to claim 1, characterized in that behind the sample (3) with an uneven surface, in the area between the specimen (3) and the imaging detector (7), there is arranged at least one pattern object (8) with known dimensions, whereupon for each focal point an image of the attenuation of the bremsstrahlung and/or fluorescent X-ray radiation (6) is recorded, showing the structure of the sample (3) and of the known pattern object (8), from the size of the image of attenuation of X-ray radiation (6) in the pattern object (8), using radiation geometry, the distance of the focal point from the sample is calculated and subsequently, after recording the images of all focal points, a 3D model of the surface of the sample (3) and/or a 3D model of the volume of the sample (3) is modeled.

3. A device (9) for X-ray nano-radiography and nanotomography using a method according to claim 1, comprising a scanning electron microscope (1) consisting of a source (10) of electron beam (2), of electron optics (11) for focusing the electron beam (2) to a point on the scanned surface of the sample (3), of at least one detector (5) for detecting reflected and secondary particles (4), and further comprising a control unit (12), characterized in that the point on the sensed surface of the sample (3) is the focal point of emission of bremsstrahlung and fluorescent X-ray radiation (6), behind the sample (3) there is arranged at least one imaging detector (7) for detecting the attenuation of the bremsstrahlung and fluorescent X-ray radiation in the sample (3), which is connected to a control unit (12).

4. A device according to claim 3, characterized in that the control unit (12) comprises at least one module from the group of modules (13) for storing data, a calculation module (14), a display module (15), a recording module (16), and a distribution module (17).

5. A device according to claim 3, characterized in that between the sample (3) and the imaging detector (7) there is arranged at least one pattern object (8) with known dimensions, and the control unit (12) is adapted to evaluate the magnification of the image of this sample captured through the attenuation of the intensity of bremsstrahlung and fluorescent X-ray radiation (6).

6. A device (9) for X-ray nano-radiography and nanotomography using a method according to claim 2, comprising a scanning electron microscope (1) consisting of a source (10) of electron beam (2), of electron optics (11) for focusing the electron beam (2) to a point on the scanned surface of the sample (3), of at least one detector (5) for detecting reflected and secondary particles (4), and further comprising a control unit (12), characterized in that the point on the sensed surface of the sample (3) is the focal point of emission of bremsstrahlung and fluorescent X-ray radiation (6), behind the sample (3) there is arranged at least one imaging detector (7) for detecting the attenuation of the bremsstrahlung and fluorescent X-ray radiation in the sample (3), which is connected to a control unit (12).

7. A device according to claim 4, characterized in that between the sample (3) and the imaging detector (7) there is arranged at least one pattern object (8) with known dimensions, and the control unit (12) is adapted to evaluate the magnification of the image of this sample captured through the attenuation of the intensity of bremsstrahlung and fluorescent X-ray radiation (6).

\* \* \* \* \*